US011461865B2

(12) United States Patent
    Hager

(10) Patent No.: US 11,461,865 B2
(45) Date of Patent: Oct. 4, 2022

(54) SYSTEMS AND METHODS FOR SAFE SOCIAL GATHERINGS DURING A CONTAGIOUS PANDEMIC

(71) Applicant: Tristan Carson Hager, Houston, TX (US)

(72) Inventor: Tristan Carson Hager, Houston, TX (US)

( * ) Notice: Subject to any disclaimer, the term of this patent is extended or adjusted under 35 U.S.C. 154(b) by 0 days.

(21) Appl. No.: 17/019,349

(22) Filed: Sep. 13, 2020

(65) Prior Publication Data
    US 2021/0366071 A1    Nov. 25, 2021

Related U.S. Application Data

(60) Provisional application No. 63/029,379, filed on May 22, 2020.

(51) Int. Cl.
    | | |
    |---|---|
    | *G06Q 50/26* | (2012.01) |
    | *G16H 10/40* | (2018.01) |
    | *G16H 50/30* | (2018.01) |
    | *G06Q 50/00* | (2012.01) |
    | *G16H 10/60* | (2018.01) |
    | *G16H 50/80* | (2018.01) |
    | *G07C 9/37* | (2020.01) |
    (Continued)

(52) U.S. Cl.
    CPC ....... *G06Q 50/265* (2013.01); *G06Q 30/0185* (2013.01); *G06Q 50/01* (2013.01);
    (Continued)

(58) Field of Classification Search
    CPC .. G06Q 50/265; G06Q 50/01; G06Q 30/0185; G16H 10/60; G16H 50/80; G16H 50/30
    See application file for complete search history.

(56) References Cited

U.S. PATENT DOCUMENTS

2002/0013794 A1\* 1/2002 Carro .................... H04L 9/0662
                                                    715/205
2005/0256841 A1\* 11/2005 Rawat .................... G06Q 40/04
                        (Continued)

OTHER PUBLICATIONS

Wilson K, Atkinson KM, Bell CP. Travel Vaccines Enter the Digital Age: Creating a Virtual Immunization Record. Am J Trap Med Hyg. 2016; 94(3):485-488. doi: 10.4269/ajtmh. 15-0510 (Year: 2016).\*
(Continued)

*Primary Examiner* — Gabrielle A McCormick
*Assistant Examiner* — Maame Ofori-Awuah
(74) *Attorney, Agent, or Firm* — Shah IP Law, PLLC

(57) ABSTRACT

The disclosure is generally directed to systems and methods for obtaining and evaluating a test result report in real-time so as to determine an entry status of an individual into the establishment. In an example embodiment, a method involves an entry verification apparatus executing actions such as: receiving digital data associated with the individual; obtaining a test result report that provides an indication whether the individual is currently infected, previously infected, or not infected, by a viral pathogen; evaluating digital data and/or a machine-readable element of the test result report to verify an identity of the individual and an authenticity of the test result report; converting non-standardized information contained in the test result report into standardized information; obtaining entry requirements for enabling entry into the establishment; analyzing the standardized information to determine whether entry requirements are met; and determining an entry status based on the entry requirements being met.

13 Claims, 6 Drawing Sheets

(51) Int. Cl.
*G06Q 30/00* (2012.01)
*G06V 30/414* (2022.01)

(52) U.S. Cl.
CPC ............ *G06V 30/414* (2022.01); *G07C 9/37* (2020.01); *G16H 10/40* (2018.01); *G16H 10/60* (2018.01); *G16H 50/30* (2018.01); *G16H 50/80* (2018.01)

(56) References Cited

U.S. PATENT DOCUMENTS

| | | | |
|---|---|---|---|
| 2015/0227945 A1* | 8/2015 | Shea, III | G06Q 30/018 705/317 |
| 2017/0177796 A1* | 6/2017 | Sellars | G16H 10/60 |
| 2018/0119137 A1* | 5/2018 | Matsuguchi | C12Q 1/6827 |
| 2019/0043148 A1* | 2/2019 | Vemury | G06K 19/06112 |
| 2019/0115111 A1* | 4/2019 | Mesidor | G16H 80/00 |
| 2019/0372968 A1* | 12/2019 | Balogh | H04L 63/0861 |
| 2020/0241769 A1* | 7/2020 | Dain | G06F 3/064 |
| 2020/0279464 A1* | 9/2020 | Llewelyn | G09G 5/02 |
| 2020/0372743 A1* | 11/2020 | Miller | G07C 9/257 |

OTHER PUBLICATIONS

M. Eisenstadt, M. Ramachandran, N. Chowdhury, A. Third and J. Domingue, "COVID-19 Antibody Test/Vaccination Certification: There's an App for That," Preprint Manuscript, pp. 1-26, 2020, https://arxiv.org/abs/2004.07376v1 (Year: 2020).*

* cited by examiner

SYSTEMS AND METHODS FOR SAFE SOCIAL GATHERINGS DURING A CONTAGIOUS PANDEMIC

CROSS-REFERENCE TO RELATED APPLICATIONS

The present application claims priority to U.S. Provisional Patent Application No. 63/029,379 filed May 22, 2020, and entitled "Systems and Methods for Safe Social Gatherings During a Contagious Pandemic," which is hereby incorporated by reference in its entirety as if fully set forth herein.

BACKGROUND

Field of the Art

The present invention is related to a systems and methods for retrieving medical information and real-time evaluating of the retrieved data to enable entry of an individual into the establishment, and/or for other purposes.

Discussion of the State of the Art

The COVID-19 pandemic created by the SARS-Cov-2 coronavirus is the latest and the most dramatic example of a contagious disease that has immobilized a significant portion of the economy around the world. Other, recent outbreaks, such as the 2002 SARS epidemic, the swine flu epidemic, the 2012 MERS epidemic, the 2014 West Africa Ebola epidemic, and the 2015 Zika virus epidemic also affected the macro and micro economies of various parts of the world in varying degrees.

In addition to the medical costs and the human costs, these epidemics damage the economy by causing a significant and sustained decline in in-person contact, as well as a decline in social gatherings and communal activities. Often, people who are not infected do not feel safe in attending social gatherings and/or may limit discretionary spending associated with social gatherings if they believe that the risk of contracting a contagious disease is sufficiently high. However, currently, there is no way to allay these concerns and promote healthy social gatherings even as the transmission rates decline for some of the more dangerous contagious diseases.

SUMMARY

The present invention solves these problems by utilizing an entry verification apparatus of an entry verification system to obtain and evaluate a test result report in real-time and determine an entry status of an individual into the establishment. The entry verification system may be used by various types of establishments (commercial, government, private, public, etc.) to permit or deny entry to individuals who have tested positive or negative for one or more pathogens. Specifically, the present invention is for a system and a method for obtaining identification data from an individual, determining the individual's personally identifiable information from the identification data, and looking up the individual's test result data to determine whether the individual has tested positive or negative for one or more pathogens. Additional medical data may be obtained such as whether the individual received a vaccination or treatment for a particular pathogen, etc. The results may be further analyzed to determine whether the individual meets one or more criteria set forth by the establishment, such as having been tested within a predetermined threshold period of time, having received one or more particular tests, having a certain confidence threshold. This analysis is done in realtime or near-realtime to enable the establishment to make realtime or near-realtime decision about whether to let someone to enter the establishment's premises.

In one example implementation, a merchant may advertise his/her establishment as a safe space that enables safe social gatherings amongst strangers with significantly lowered risk of contracting a contagious disease. As such, the establishment may encourage patrons to enter the establishment with confidence for their health and safety.

More specifically, the present invention discloses a method for determining whether to grant entry to an individual into the establishment, the method comprising receiving, by an entry verification apparatus, digital data associated with the individual; obtaining, by the entry verification apparatus, a test result report that provides an indication whether the individual is one of currently infected by a viral pathogen, previously infected by a viral pathogen not infected by a viral pathogen, or immunized against a viral pathogen; evaluating, by the entry verification apparatus, the received digital data associated with the user and the obtained test result report to verify that the obtained test result report is associated with the individual; authenticating, by the entry verification apparatus, the obtained test result report by evaluating a machine readable element of the test result report; converting, by the entry verification apparatus, information contained in the test result report into a standardized format; obtaining, by the entry verification apparatus, entry requirements for enabling entry into the establishment; analyzing, by the entry verification apparatus, the standardized information and the entry requirements to determine whether the entry requirements are met; and determining, by the entry verification apparatus, an entry status based on whether the entry requirements are met.

In one embodiment, authenticating the obtained test result report comprises evaluating at least a portion of metadata associated with the digital data. Moreover, verifying the identity of the individual comprises: identifying a type of an identification provided by the individual; when the identification is issued by a government agency, extracting data from the identification and evaluating the data to verify the identity of the individual; when the identification is issued by a private entity, verifying an authenticity of the identification; and upon confirming the authenticity, verifying the identity of the individual. In one embodiment, evaluating the machine-readable element of the test result report comprises evaluating a spatial disposition and/or a modification of a text character in a document. In one embodiment, the document may be comprised of manually-entered text and the text character is a portion of the manually-entered text. In one embodiment, converting to a standardized comprises identifying information contained in a portion of the test result report and tagging that information with a standardized tag. The standardization process may, in one embodiment, be comprised of arranging elements of a name of the individual as provided in the test result report, re-arranging elements of a date as provided in the test result report, and replacing a first label of a test result in the test result report with a second label. The method may further comprise obtaining, by the entry verification apparatus, a permission from the individual for obtaining the test result report.

The method for granting entry may be further comprised of receiving, by an entry verification apparatus, a first digital data associated with an identity of the individual; evaluating, by the entry verification apparatus, the first digital data to verify the identity of the individual; receiving, by the entry verification apparatus, a second digital data associated with a social behavior of the individual; evaluating, by the entry verification apparatus, the second digital data to determine a risk factor associated with the social behavior of the individual having caused exposure to a viral pathogen; obtaining, by the entry verification apparatus, entry requirements for enabling entry into the establishment; and determining, by the entry verification apparatus, an entry status based on whether the risk factor exceeds a threshold value that is defined in the entry requirements.

The method may be further comprised of transmitting to a controller of a gate entry system, an activation signal for automatically opening a gate when the risk factor of the individual is below the threshold value defined in the entry requirements. In one embodiment, the second digital data contains information provided by a social media platform. In one embodiment, the information provided by the social media platform is contained in a digital image format and/or a text format. In one embodiment, the method may be further comprised of obtaining a test result report that provides an indication whether the individual is one of currently infected, previously infected, or not infected by a viral pathogen; evaluating a third digital data and/or a machine-readable element of the test result report to verify an authenticity of the test result report; and analyzing the test result report to determine the entry status further based on whether the individual is one of currently infected, previously infected, or not infected by a viral pathogen. In one embodiment, the method may be further comprised of converting non-standardized information contained in the test result report into a standardized format; and analyzing the standardized information to determine whether the entry requirements are met.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
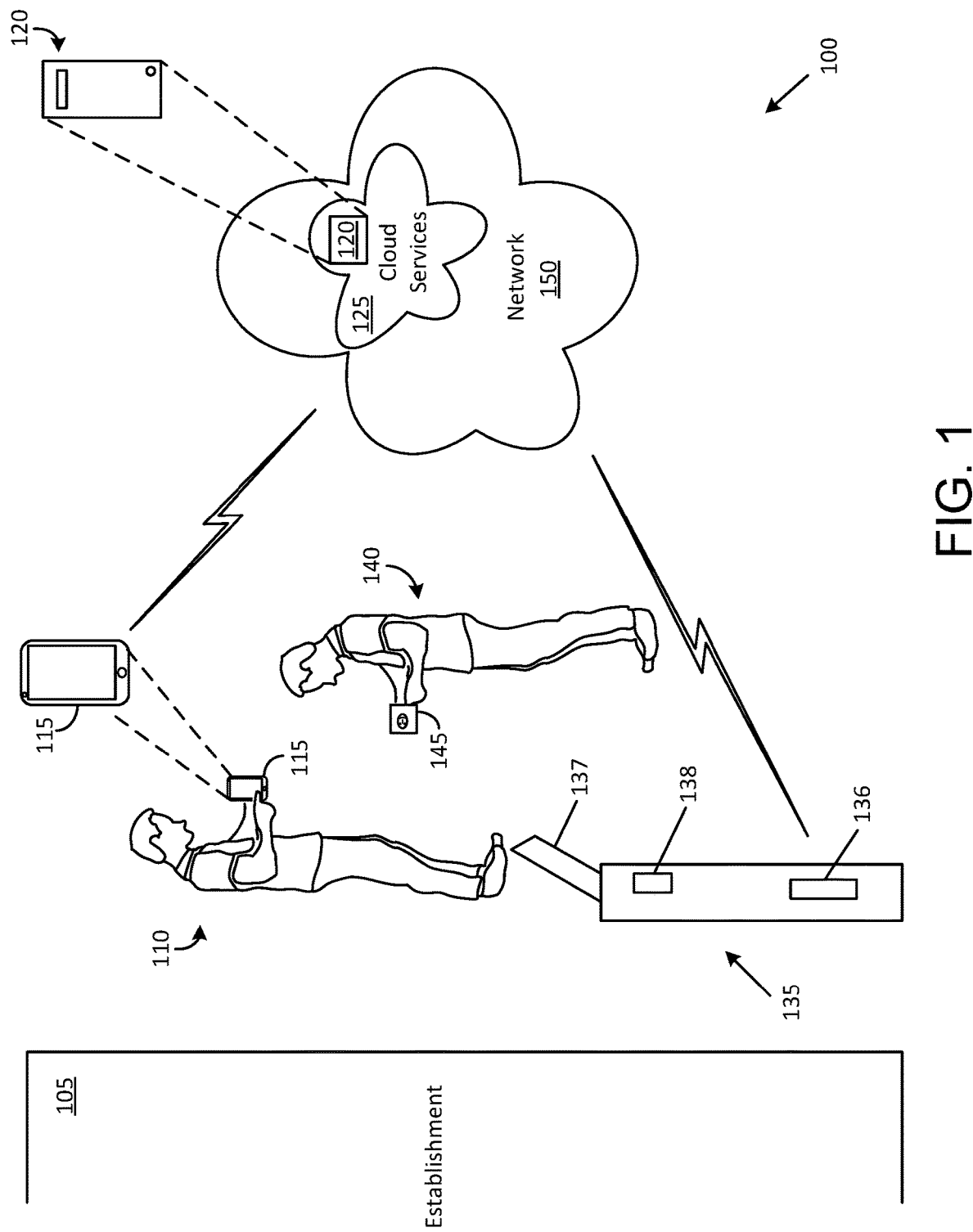
FIG. 1 illustrates an exemplary entry verification system in accordance with an embodiment of the disclosure.

The inventive systems and methods (hereinafter sometimes referred to more simply as "system" or "method") are described below in reference to FIGS. 1-9. As described herein, the inventive systems and methods enable safe social gatherings amongst strangers who may not otherwise know whether others in the same establishment have contracted a virus and/or may be contagious with respect to one or more viruses.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

FIG. 1 illustrates an exemplary entry verification system 100 in accordance with an embodiment of the disclosure. The entry verification system 100 includes an entry verification apparatus 120 that may be included as a component of cloud services 125 hosted via a network 150. In an exemplary embodiment, an individual 140 seeks entry in to the establishment 105 by interacting with a person who has been designated as an entry monitor 110 for controlling entry into the establishment 105. The establishment 105 can be any of various types where multiple people congregate, such as, for example, a restaurant, a store, a housing complex, a hospital, a nursing home, an old age home, a school, a college, a bar, a mall, a place of worship, a sports arena, a concert venue, a government office, a private office, premises of a company, a warehouse, a factory, a transport facility, a manufacturing facility, a production facility, and/or a vehicle (including rentable vehicle, a ride share vehicle, etc.). The individual 140 may carry a form of identification (ID) 145 that he/she may present to a person who works as an entry monitor 110. The entry monitor 110 may execute an entry verification procedure in accordance with the disclosure for allowing or disallowing the individual 140 into the establishment 105.

The ID 145 may be any of various types of objects or documents that may be submitted to the individual 110 when requesting entry into the establishment 105. A non-exhaustive list of example objects or documents may include a driver's license, a passport, a badge and/or a document) issued by a government agency, a badge and/or document issued by the establishment 105, a badge and/or a document issued by a private company, a badge and/or a document issued by a public company.

In one exemplary scenario, the individual 140 presents the ID 145 to the entry monitor 110. The entry monitor 110 may operate a user device 115, which can be any of various types of devices, such as, for example, a smartphone, a tablet computer, a notebook computer, or a desktop computer. The entry monitor 110 may use the user device 115 to convert information contained in the ID 145 into digital data. For example, the entry monitor 110 may use the user device 115 to capture an image of the ID 145, which, for example, may be a driver's license containing a photograph 146 of the individual 140. The user device 115 may convert the ID 145 into digital data such as, for example, in the form of a JPEG file. The digital data may thus include information in the form of the photograph 146 and text contained in the ID 145 (name, address, license number, date of birth, etc.). In another case, the entry monitor 110 may manually enter information contained in the ID 145 (such as, for example, name, address, license number, date of birth, etc. of the individual 140), which is then converted into digital data by the user device 115. In yet another case, the entry monitor 110 may manually enter information contained in the ID 145, which may be a document, for example, and also use the user device 115 to capture a photograph of the individual 140. The photograph and the entered information may be converted into digital data by the user device 115.

The entry monitor 110 may then request the individual 140 to submit a test result report if the individual 140 has one to submit. The entry monitor 110 may further request the individual 140 to grant permission for the entry verification system 100 to obtain the test result report if the individual 140 does not have one available for submitting. This action may be carried out is various ways such as, for example, requesting the individual 140 to sign a waiver that is crafted in compliance with Health Insurance Portability and Accountability Act (HIPPA) regulations. The test result report may be provided in the form of a paper document submitted by the individual 140 and/or in the form of digital content (image, email, fax, an attachment to an email, etc.) contained in (and/or otherwise accessed by) a user device (not shown) of the individual 140. The user device of the individual 140 may be any device such as, for example, a smartphone, a tablet computer, a portable computer, a phablet (phone plus tablet computer, or any smart device such as smartwatch. In one embodiment, the individual 140 may submit his or her test results to the verification apparatus 120 directly or indirectly. For example, in one embodiment of the invention, the individual 140 may use an application that associated with the verification apparatus 120 and executing on the user device of the individual 140 to upload or grant access to his or her test results.

In embodiments where appropriate, the digital data entered into the user device 115 of the entry monitor 110 is transmitted to the network 150 through a communication medium such as, for example, a cellular link, a wireless link, a WiFi link, a wired link, and/or an optical link. The digital data is routed through the network 150 to the entry verification apparatus 120 that is included in the cloud services 125. The entry verification apparatus 120 may execute an entry verification procedure to determine an entry status of the individual 140 to the establishment 105. In an example implementation, the entry verification procedure may involve various operations such as receiving the digital data transmitted by the user device 115. The digital data can include the identification details of the individual 140 and may also include the test result report (if the individual 140 has submitted such a report). In some cases, the individual 140 may not have a test result report on his/her person, or the entry verification apparatus 120 may be configured to obtain the test result report from a source other than the individual 140. For example, the entry verification apparatus 120 may be configured to obtain the test result report of the individual 140 from a testing laboratory such as LabCorp®, for example. Obtaining the test result from a source other than the individual 140 may confer a certain level of authenticity to the test result report in at least some cases.

However, the entry verification apparatus 120 is further configured to evaluate the digital data obtained from the user device 115 of the entry monitor 110, and/or user device of the individual 140 and/or a testing laboratory (which may also include a results provider associated with the testing laboratory) in order to verify/authenticate the identity of the individual 140 and also to evaluate the test result report to verify the authenticity of the test result report. Verifying the identity of the individual may be performed in various ways. For example, the entry verification apparatus 120 may verify the identity of the individual 140 by cross-checking information contained in a driver's license submitted by the individual 140 with data obtained from a government licensing authority. Machine-readable elements that may be present in the driver's license may also be evaluated. Verifying the authenticity of the test result report may be performed in various ways such as by evaluating machine-readable elements and digital data contained in the test result report.

In an exemplary implementation, the entry verification apparatus 120 may verify the authenticity of the test result report by evaluating digital data associated with the test result report. For example, the entry verification apparatus 120 may verify the authenticity of the test result report by evaluating metadata associated with a file containing the test result report in the form of digital data. The test result report may be included in the file in any of various formats such as, for example, in the form of a portable document format (pdf) document, an extensible markup language (xml) document, a JavaScript Object Notation (JSON) file, a scraping from a website, and/or a spreadsheet. The entry verification apparatus 120 may process the digital data of the file to determine if an entry in the test result report has been tampered with, such as, for example, to change a positive result of an infection to a negative result. Such tampering typically generates a digital footprint that can be detected by the entry verification apparatus 120 but is indiscernible to human eyes and is inaccessible to a human being without the use of a computer.

As another example, the entry verification apparatus 120 may verify the authenticity of the digital document by evaluating one or more data points and/or pixels that may be contained or rendered with the digital document. In one embodiment, the test results may be available in the form of text entered into a fillable form (a fillable pdf form, for example) into which an individual may make manual entries. The authenticity evaluation may include identifying any discrepancies in spatial disposition of one or more text characters. The spatial disposition may be characterized by features such as, for example, a text character that is located on the document at a spot other than expected, missing one or more punctuation marks, displacement of a character in one or more directions, and transposition of characters or words. In one implementation, such features may be detected by using a template document. The template document may be generated in various ways such as, for example, by evaluating crowdsourced filled documents from a number of people, examining filled document in historical records, and/or based on information obtained from an author/originator of an unfilled document. The level of granularity applied in identifying spatial dispositions may be too high for execution of this procedure by a human being. For example, in some cases, the spatial dispositions may be measured in the order of millimeters or microns.

As yet another example, the entry verification apparatus 120 may process the digital data of the file by examining elements that may not be readily discernible to humans and/or interpretable by humans, such as, for example, an invisible watermark, a seal with intricate content, a barcode, a UPC symbol, a holographic icon etc.

The test result report may provide various types of information and may particularly include an indication whether the individual is currently infected, previously infected, not infected, and/or immunized against or for a viral pathogen. However, various testing organizations may utilize various types of descriptions and terminology in their test result reports. For example, a first testing laboratory may refer to an antigen test result using a "xxx" label and a second testing laboratory may refer to the same antigen test result using a "yyy" label. In other embodiments, the test results may be printed on a PDF form. In other embodiments yet, the test results may be contained in a results documents and/or a digital file in a variety of different form and/or file formats. The test results may be presented in the form of check marks, "X" marks, radio selection elements, in the form of specific user interface elements within a document and/or a file, etc., and may be present in a variety of different areas or portions of the results document or file. In another example, the type of test used to test a medical condition and/or a quantification of the test results may differ from one testing organization to another. The entry verification apparatus 120 may convert, if warranted, non-standardized information contained in one or more test result reports into standardized information that can be used to compare and/or evaluate test results from multiple testing organizations. A few examples associated with converting non-standardized information contained in the test result report into standardized information can include: re-arranging elements of a name of the individual as provided in the test result report (such as by placing a last name ahead of a first name and adding a comma after the last name), re-arranging elements of a date as provided in the test result report (swapping a position of a day and a month, for example), and replacing a first label of a test result with a second label ("xxx" label of a test with "yyy" label for the same test).

Currently, it is very difficult for various agencies to monitor and track compliance with various tests in any meaningful way or to track real-time or near-real-time compliance because tests results providers are often disparate and unconnected to agencies that may want to act or track compliance with the results. Moreover, test results are often stored locally in a non-standard format selected by whichever hardware or software platform is in use in the testing facility's local office (or stored locally on a user device associated with the individual 140). Moreover, test results are often siloed and inaccessible to establishments 105 that may want access to these test results because of patient confidentiality rules. Moreover, because test results are often in unsecured documents, it is all but impossible to verify the authenticity of the results or the document for meaningful compliance monitoring. It is therefore difficult for test results providers to share updated information about a patient or individual's 140 condition with others due to the above challenges. This can lead to problems with accessing data, reading the data, verifying the data, among others. In addition, in contrast to other types of medical data, test results data is time-sensitive in nature and is reliable for only a certain, short period of time. As such, the real-time and continuous nature of the present invention is important to enable the functionality of the present invention. Moreover, an individual 140 may get a test from a variety of different testing facilities that may use a variety of different testing procedures, each with a potentially different recordation and storage procedures, etc. Further compounding the difficulty, the individual 140 may be vaccinated by a physician or an entirely unrelated provider who may store and present data in an entirely different way and/or format. Currently, none of the available systems can continually monitor a patient's test and immunization records for updated information, which is often-times incomplete since records are in separate locations, are not timely or readily-shared, or cannot be consolidated due to format inconsistencies as well as rank ordering reliance on test result data for when more than one test results are available.

To solve this problem, applicant has invented a network-based compliance monitoring system that collects, converts and consolidates test result information from various testing providers, and/or vaccination providers into a standardized format, stores it in network-based storage devices, and enables real-time or near-real-time access in accordance with the disclosure herein.

The entry verification apparatus 120 may also examine the rest result report to identify a date on which a test was conducted. If the testing was carried out on a date that is earlier than a cutoff date, the entry verification apparatus 120 may deem the test result invalid. For example, if a test was carried out before a cutoff date then the entry verification apparatus 120 may deem the test result invalid and may deny entry to the individual 140. The cutoff date may be obtained from a variety of different sources as described in greater detail below, including from the establishment 105.

As a further part of the example scenario described above, the entry verification apparatus 120 may obtain entry requirements from various sources for enabling the individual 140 to enter the establishment 105. The nature of the entry requirements can vary depending on the nature of the establishment 105. A commercial establishment such as a store or a restaurant may have a somewhat less stringent set of entry requirements than, for example, a hospital or a nursing home. The entry requirements may be stored in various places such as, for example, in a computer that is a part of the cloud services 125 and/or in a computer located on the premises of the establishment 105. In one embodiment, the entry requirements may be comprised of a cutoff date or date ranges.

The entry verification apparatus 120 may then evaluate the information derived from the test result report in view of the entry requirements. The results of the evaluation may be transmitted from the entry verification apparatus 120 to the user device 115 of the entry monitor 110. In one embodiment, the results may be comprised of permit entry or deny entry. The entry monitor 110 may refer to the results of the evaluation and take any of various types of actions. In one scenario, the entry monitor 110 may allow the individual 140 to enter the establishment 105 if the evaluation result indicates that the individual 140 meets the entry requirements (i.e. has tested negative for a viral pathogen within a cutoff period or if the individual is immunized or vaccinated against a viral pathogen or communicable disease, etc.). In another scenario, the entry monitor 110 may prohibit the individual 140 from entering the establishment 105 if the evaluation result indicates that the individual 140 does not meet entry requirements (i.e. the individual 140 is currently infected by the viral pathogen, test data in inconclusive, test results are prior to a cutoff date, etc.). The entry monitor 110 may opt to convey the result of the evaluation to the individual 140 or may refrain from doing so based on various guidelines that may be provided by the establishment 105 or other authorities.

In another exemplary embodiment, the individual 140 seeks entry into the establishment 105 by interacting with a controller 136 that is a part of an automated gate 135. In this exemplary embodiment, the individual 140 may, for example, be seated in a vehicle that is pulled up next to the automated gate 135. The automated gate 135 includes a lift bar 137 that is operable under control of the controller 136.

In an exemplary scenario, the individual 140 presents the ID 45 to an information input element 138 of the automated gate 135. The information input element 138 may be a card reader, for example, and the ID 45 may be a smartcard containing a smart chip, a card having a magnetic stripe containing information, or a touchless card. Information contained in the ID 45 in the form of digital data is automatically transmitted by the controller 136 to the network 150 through a communication medium such as, for example, a cellular link, a wireless link, a WiFi link, a wired link, and/or an optical link. The digital data is routed through the network 150 to the entry verification apparatus 120. In some implementations, the information input element 138 may further include an imaging device that is configured to capture an image of the individual 140. The image may also be automatically transmitted by the controller 136 to the entry verification apparatus 120 via the network 150.

The information input element 138 may further include a voice interface. The voice interface may include a voice synthesizer that operates under control of the controller 136 to output a voice message requesting the individual 140 to submit a test result report if the individual 140 has one to submit. The voice message may further request the individual 140 to grant permission for the entry verification system 100 to obtain the test result report if the individual 140 does not have one available for submitting. This action may be carried out is various ways such as, for example, requesting the individual 140 to sign a waiver that is crafted in compliance with Health Insurance Portability and Accountability Act (HIPPA) regulations. The test result report may be provided to the information input element 138 in the form of a paper document (the imaging device may capture an image of the paper document) and/or in the form of digital content (image, email, fax, etc.) that is wirelessly transmitted to the information input element 138 by a user device (not shown) of the individual 140. The controller 136 may then automatically transmit the test result report in the form of digital data to the entry verification apparatus 120 via the network 150.

The entry verification apparatus 120 may execute an entry verification procedure to determine an entry status of the individual 140 to the establishment 105. The entry verification procedure in this embodiment may be substantially similar to the entry verification procedure described above. The evaluation results of the entry verification procedure may be transmitted from the entry verification apparatus 120 to the controller 136. The controller 126 may make a determination whether to allow the individual 140 to enter the establishment 105 based on the evaluation results. If the evaluation result indicates that the individual 140 is not currently infected by the viral pathogen (for example, COVID-19) and has not been infected before by the viral pathogen, or has been inoculated against a relevant viral pathogen, then, the controller 136 may lift the lift bar 137 and allow the individual 140 to enter the establishment 105. If the evaluation result indicates that the individual 140 is currently infected by the viral pathogen, the controller 136 may prohibit the individual 140 from entering the establishment 105 by refusing to raise the lift bar 137. In an example implementation, a voice message may be provided to the individual 140 explaining the reason that the lift bar 137 has not been lifted.

In one embodiment, the inventive network-based compliance monitoring system that collects, converts and consolidates test result information from various testing providers, and/or vaccination providers into a standardized format, stores it in network-based storage devices, and enables real-time or near-real-time access in accordance with the disclosure herein. More specifically, the entry verification apparatus 120 generates messages notifying the individual 140 and/or the establishment 105 whenever the individual's exposure status in relation to a communicable disease or a viral pathogen is updated (i.e. when new test results are updated, when new vaccination or immunization records are available, or cutoff dates are crossed). The method provides a graphical user interface (GUI) by a entry verification apparatus 120, which is hardware or a combination of both hardware and software. In one embodiment, the individual 140, an establishment 105, an entry monitor 110, testing provider and/or vaccination provider is given remote access through the GUI to view or update information about test result data and/or relevant vaccination information using their own local device (e.g., a personal computer or wireless handheld device as described above). When a participant wants to update the records, they can input the update in any format used by the user's local device. Whenever the individual 140 information is updated, it will first be converted into the standardized format and then stored in a standardized format on one or more of the network-based storage devices (not illustrated in FIG. 1 but the specific implementation would be readily apparent to a person of ordinary skill in the art). After the updated information about the patient's condition has been stored in the network-based storage devices, the entry verification apparatus 120, which is connected to the network-based storage devices, immediately generates a message containing the updated information about the patient's condition in relation to a contagious disease or a viral pathogen. This message is transmitted in a standardized format over the computer network to one or more of the individual 140, verification services 120, and/or the user device 115 of the entry monitor 110 that have access to the individual's 140 information so that one or more participants can quickly be notified of any changes without having to manually look up or consolidate all of the providers' updates. This ensures that at entry point, relevant parties always have immediate notice and access to changes so they can provide safe and secure access to those who may want to access an establishment 105 in a safe environment. The message can be in the form of an email message, text message, or other type of message known in the art.

In one embodiment, the inventive system may be comprised of the entry verification apparatus 120 and the user device associated with the individual 140. In this embodiment, the individual 140 may download an application that is associated with the entry verification apparatus 120 and executes on the user device of the individual 140 (or the individual 140 may navigate to a website or a portal associated with the entry verification apparatus 120). The individual may submit his or her personal identifier (ID), and test result data (in the form of a document upload, in the form of permitting access to his or her test result data that may be stored by a test provider and/or a vaccination provider, etc.). The entry verification apparatus 120 may access the relevant data and may perform authentication and verification, and permissioning steps disclosed herein. In this embodiment, the entry requirements including the cutoff date may be set based on a consensus (i.e. universal time frame) that may be associated with gatherings of various sizes and/or types. If the individual 140 is permitted to enter the establishment 105, then the entry verification apparatus 120 may generate user interface elements which can be delivered for display on the computing device of the individual 140. In this instance, the individual 140 may display the UI elements to an entry monitor and gain access to the establishment 105 in this manner.

It must be understood that the user device 115 referred to above, may generally include a computer or computing device including functionality for communicating (e.g., remotely) over the network 150. Various user devices such as, for example, the user device 115 and the user device carried by the individual 140, may be included in the entry verification system 100 in various forms. As such, a user device may be a server, a desktop computer, a laptop computer, personal digital assistant (PDA), an in- or out-of-car navigation system, a smart phone or other cellular or mobile phone, or mobile gaming device, among other suitable computing devices. User device 115 may execute one or more client applications, such as a web browser (e.g., Microsoft Windows Internet Explorer, Mozilla Firefox, Apple Safari, Google Chrome, and Opera, etc.), or a dedicated application to submit digital data, or to make prediction queries over a network 150.

In particular embodiments, the user device 115 may be an electronic device including hardware, software, or embedded logic components or a combination of two or more such components and capable of carrying out the appropriate functions implemented or supported by the user device 115. For example, and without limitation, the user device 115 may be a desktop computer system, a notebook computer system, a netbook computer system, a handheld electronic device, or a mobile telephone. The present disclosure contemplates any user device 115. The user device 115 may enable a network user at the user device 115 to access network 150. The user device 115 may enable its user to communicate with other users at other user devices.

The user device 115 may have a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. The user device 115 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 115 one or more Hyper Text Markup Language (HTML) files responsive to the HTTP request. The user device 115 may render a web page based on the HTML files from server for presentation to the user. The present disclosure contemplates any suitable web page files. As an example, and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 115 may also include an application that is loaded onto the user device 115. The application obtains data from the network 150 and displays it to the user within an application interface.

Exemplary user devices are illustrated in some of the subsequent figures provided herein. This disclosure contemplates any suitable number of user devices, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing system may perform at different times or at different locations one or more steps of one or more methods described or illustrated herein, where appropriate.

Network 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or a combination of two or more such networks. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various elements described herein.

In particular embodiments, the entry verification apparatus 120 may be a unitary server or may be a distributed server spanning multiple computers or multiple datacenters. Systems, engines, or modules associated with the entry verification apparatus 120 may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to client devices or other devices in response to HTTP or other requests from clients devices or other devices. A mail server is generally capable of providing electronic mail services to various client devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiment, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

Figure 2:
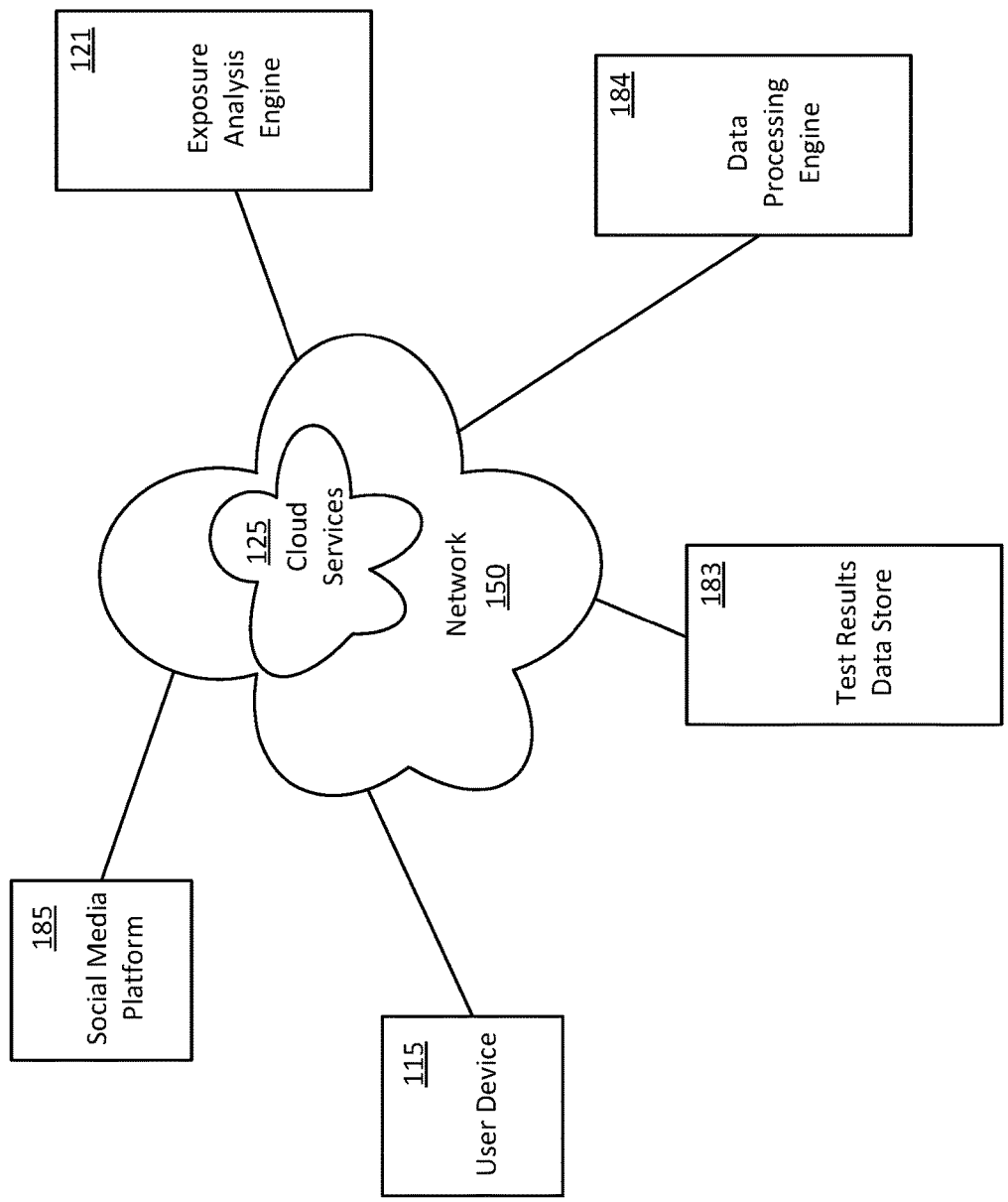
FIG. 2 illustrates some elements that may be included in the entry verification system shown in FIG. 1.

FIG. 2 illustrates some exemplary elements that may be included in the entry verification system 100 in accordance with another embodiment of the disclosure. The exemplary elements may include a data processing engine 184, a test results data store 183, an exposure analysis engine 121 and a social media platform 185. In an exemplary embodiment, some or all of the data processing engine 184, the test results data store 183, and the exposure analysis engine 121 may be provided in the entry verification apparatus 120. In another embodiment, at least the test results data store 183 may be provided in a device other than the entry verification apparatus 120. Such a device is communicatively coupled to the network 150 to enable for communications with various other devices including the entry verification apparatus 120.

The data processing engine 184 refers to a computing engine that processes the digital data that is captured and/or obtained by the user device 115. In one embodiment, the data processing engine 184 receives, for example, an image of a user's identifier (such as the photograph 146 of the individual 140 on the ID 145), and processes the received data to identify an ID type. In one instance, the data processing engine 184 may determine whether the image is of a government issued license, or for example, an employer issued ID card. The data processing engine 184 may also identify the name and other identifying information that may be present in the ID 145. In one embodiment, the user name information may be provided to the exposure analysis engine 121 to determine whether the user 140 has taken a test associated with one or more viruses and/or screening protocols as described in detail below.

The exposure analysis engine 121 performs a lookup operation on the test results data store 183 to retrieve the test data that may be associated with the user 145 identified by the data processing engine 184. As described in greater detail below, the exposure analysis engine 121 may obtain a test results from the test result data store 130 and determine whether those test results would enable a user to access the establishment 105 based on the requirements set forth by the establishment. In one embodiment, the exposure analysis engine 121 may obtain the requirements set forth by the establishment and compare them against the test results data obtained from the test results data store 183. If the requirements are met, the exposure analysis engine 121 may provide an indication to the user device 115 to enable a individual 140 to enter the establishment 105.

The social media platform 185 may be any of various platforms that support social media activities of various individuals, including the individual 140 who is seeking entry into the establishment 105. A few examples of social media platform 185 may include Facebook®, WhatsApp®, Twitter®, and Snapchat®. Social media platform 185 may further include various website hosting services and chat-room platforms that support chatrooms where individuals can interact privately or publicly with each other.

In an example embodiment in accordance with the disclosure, the entry verification apparatus 120 may receive digital data from the user device 115 of the entry monitor 110 and/or from a user device of the individual 140 as described above. The entry verification apparatus 120 may then execute an entry verification procedure to determine an entry status of the individual 140 to the establishment 105. The entry verification procedure may involve various operations such as, for example, verifying/authenticating the identity of the individual 140 and determining a risk factor associated with a social behavior of the individual 140. Verifying/authenticating the identity of the individual 140 may be carried out in various ways such as by using the example procedures described above.

Determining a risk factor associated with a social behavior of the individual 140 may be carried out by accessing the social media platform 185 to obtain digital data that provides information pertaining to the social activities of the individual 140. In an example operation, the entry verification apparatus 120 may obtain digital data from Facebook® and evaluate the digital data to determine whether the individual 140 has been indulging in risky behavior that may have led to exposure of the individual 140 to a viral pathogen. Some examples of risky behavior may include violation of social distancing norms, traveling to foreign countries having high prevalence of a pandemic, and/or entering into facilities such as nursing homes, hospitals, and college fraternities. The entry verification apparatus 120 may assign a risk factor to the individual 140 based on his/her social behavior. In one example implementation, the entry verification apparatus 120 may assign a risk factor of 1 out of 10 to the individual 140 and a risk factor of 9 out of 10 to another individual. The entry verification apparatus 120 may then determine an entry status of the individual 140 to enter the establishment 105 based on carrying out operations such as obtaining entry requirements from various sources (including information on what constitutes an acceptable risk factor) and using the entry requirements to either allow or deny the individual 140 entry into the establishment 105. In one embodiment, the entry requirements may include a threshold value of risk factor that the individual 140 must meet in order to be obtain entry into an establishment 105. If the risk factor associated with the individual 140 is above or below a threshold value, the individual may be permitted or denied entry accordingly.

Figure 3:
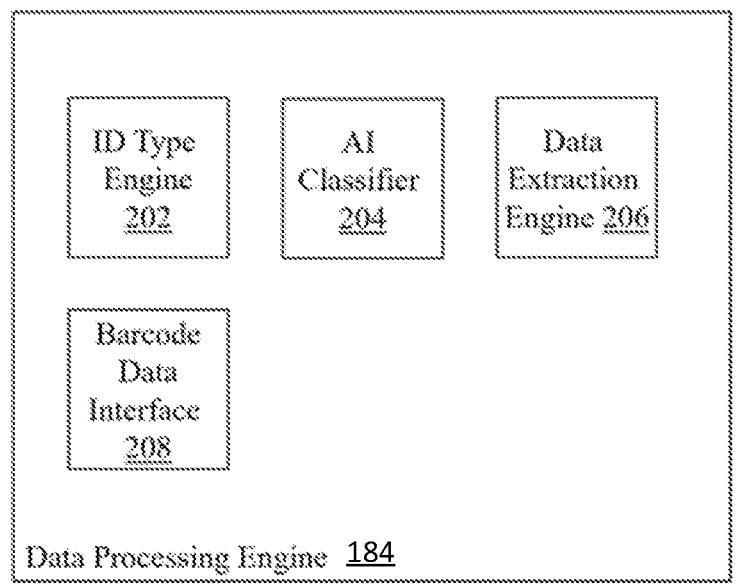
FIG. 3 illustrates some exemplary components that may be included in a data processing engine of an entry verification system in accordance with an embodiment of the invention.

FIG. 3 illustrates an exemplary embodiment of a system for enabling safe social gatherings during or after the outbreak of a contagious virus. Specifically, FIG. 3 illustrates the components of the data processing engine 184 that is described above. The data processing engine 184 may include an ID type engine 202, an artificial intelligence (AI) classifier 204, a data extraction engine 206, and a barcode data interface 208.

The ID type engine 202 determines the type of ID that the individual 140 may have provided to the user device 115 for a determination of whether the individual 140 should be allowed into the establishment 105 based on whether the individual 140 may be a carrier of a contagious disease. In one embodiment, the ID type engine 202 may determine whether the ID 145 is a government issued ID, such as a driver's license, passport, etc., a privately issued ID card, such an employee ID, student ID, etc. In another embodiment, the ID type engine 202 may also determine whether the ID 145 includes a photograph of the individual 140. If a photograph is not detected in a government issued ID, for example, an alert may be generated by the ID type engine 202. The ID type engine 202 may use available technologies to determine whether a provided ID card is a government issued ID, including, but not limited to an AI analysis engine, a special barcode reader/scanner that may process barcode data that may be available on an ID card.

The barcode data interface 208 may process barcode information that is associated with a government issued ID card and may obtain relevant information about the individual/user who is seeking entry into the establishment 105. In one embodiment, the barcode data may be in the form of PDF417 barcodes, which are generally universal in North American driver's license. These barcodes follow specifications laid out by the American Association of Motor Vehicle Administrators (AAMVA), and can encode a lot of information, including the individual's name and other information that may be used to retrieve medical information associated with the individual 140.

The AI classifier 204 may apply AI classification techniques to ID cards that are determined to be privately issued, by, for example, employers, educational institutes, etc. In one embodiment, the AI classifier 204 may be comprised of a training dataset that is comprised of a variety of different privately issued ID cards. A variety of different classification algorithms may be used, as would be apparent to a person of ordinary skill in the art, to determine whether and where relevant information is printed onto the privately issued card.

The data embodied in the ID card may be extracted by the data extraction module 206 for processing by the exposure analysis engine 121. In one embodiment, the data extraction module 206 extracts name and/or address data associated with the individual 140 who wishes to gain entry into the establishment 105. The extracted data may be further processed such that the data may be used by a lookup system to retrieve additional medical and/or test data associated with the individual 140.

Figure 4:
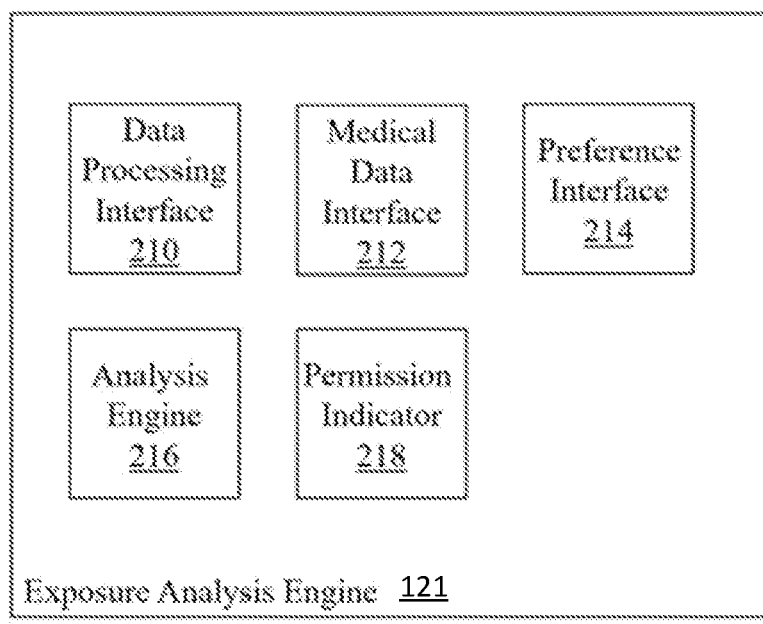
FIG. 4 illustrates some components that may be included in an exposure analysis engine of an entry verification system exemplary in accordance with an embodiment of the invention.

FIG. 4 illustrates the exposure analysis engine 121 that is illustrated in FIG. 2. The exposure analysis engine 121 retries the medical/test data associated with the individual 140 and determines whether the individual 140 should be permitted entry into the establishment 105. The exposure analysis engine 121 may include a data processing interface 210, a medical data interface 212, a preference interface engine 214, an analysis engine 216, and a permission indicator 218.

The data processing interface 210 interfaces with the data processing engine 184 to obtain information about the individual 140, including, but not limited to, name, address, and/or other personally identifying information. In other instances, the data processing interface 210 may also interface with other computing systems and subsystems to, for example, obtain permissions provided by the individual 140 to lookup/retrieve the test result report.

The medical data interface 212 interfaces with test results data store 183 to obtain the test result report of the individual 140 that has been retrieved by the data processing interface 210. In one embodiment, the medical data interface 212 may supply additional permissions and validation that may be required in order to obtain data from the test results data store 183. For example, in some cases, the test results data store 183 may require a user signature or pre-supplied permissions to enable the medical data interface 212 to access the data that is associated with the individual 140 in the test results data store 183. In one embodiment, the medical data interface 212 may obtain relevant test results as well as associated data, including, but not limited to metadata. The additional data may be comprised of the date the test was administered, the type of test that was administer (for example, a nasal or oral swab test, a blood test, etc.). The test results data store 183 may also include vaccination information, including the type of vaccine that was administered and the date of administration. This data may be used, as described in more detail below, to enable or prevent entry of the individual 140 to the establishment 105.

The preference interface engine 214 obtains entry requirements that may be set forth by the establishment 105. Entry requirements may vary and may include, for example, that a particular type of test to have been administered to a user, at a particular time, and with a particular type of results. Some establishments may, for example, require that individuals must have either a nasal/oral swab test within a previous one week in order to obtain entry. Other may only require, for example, a blood test to have been administered within the previous two weeks. In this manner, each establishment may set forth rules on who may enter an establishment in accordance with its preferences and/or preferences of various individuals (such as, for example, customers of a business) and may provide sufficient comfort to these individuals. In other embodiments, the establishment 105 may require that the individual 140 have received a vaccine for a particular virus within a predetermined time. In such embodiments, the preference engine 214 obtains the entry requirements associated with vaccines.

The analysis engine 216 compares the test results of the individual 140 against entry requirements set forth by the establishment 105. In one exemplary embodiment, the analysis engine 216 may generate a database listing the requirements obtained from the preference interface engine 214 and may further populate the database with test results data obtained from the medical data interface 212. The analysis engine 216 may perform analysis to determine if the test results meet, exceed, or do not meet the requirements obtained from the preference interface engine 214. In other embodiments, the analysis engine 216 determines whether the test results data is within a certain range of the requirements set forth by the establishment 105. The analysis engine 216 may also determine whether the test results are within a threshold range of the requirements set forth by the establishment 105. In other embodiments, the analysis engine 216 may compare vaccination data of the individual 140 against the entry requirements set forth by the establishment 105. If the individual 140 has received a vaccine for a particular contagion within a threshold period of time, then the individual 140 may be enabled to enter the establishment 105.

The permission indicator 218 may generate a positive indication if the test results of the individual 140 meet the requirements set forth by the establishment 105 as determined by the analysis engine 216. Conversely, the permission indicator 218 may generate a negative indication if the test results of the individual 140 do not meet the requirements set forth by the establishment 105 as determined by the analysis engine 216. In one embodiment, the permission indicator 218 may interface with the user device 115 and may provide the indication such that the establishment 105 may be able to make realtime decision about whether to permit or deny entry to the individual 140 who is seeking entry.

In another embodiment, the above-mentioned establishment may broadly refer to a transportation business including public transportation services as well as private/individual transportation providers. Public transportation services may be mass transit including, but not limited to, buses, trains and subways. Private/individual transportation services may be ridesharing services including, but not limited to, taxicabs, LIBER, LYFT and the like.

In this embodiment, the exposure analysis engine 140 may be used to not only provide the establishment with a result or permission indication, but may also be configured to provide both the establishment and user/patron with an indication that the driver of a ridesharing service has satisfactory test results, so that users/patrons may be confident that use of the transportation service would not pose a direct threat of exposure to a disease as a result of a driver's medical status.

In this scenario, the permission indicator 218 may be configured by the establishment to include certain test result requirements be met by its providers (e.g. drivers) in order to participate in ridesharing services. The indications from the permission indicator may be communicated via network 150 to the establishment and to multiple user devices 110 including both the user/patron and the transportation provider (e.g. driver) so that all parties involved are informed about the exposure risk associated with participation in the given service.

Figure 5:
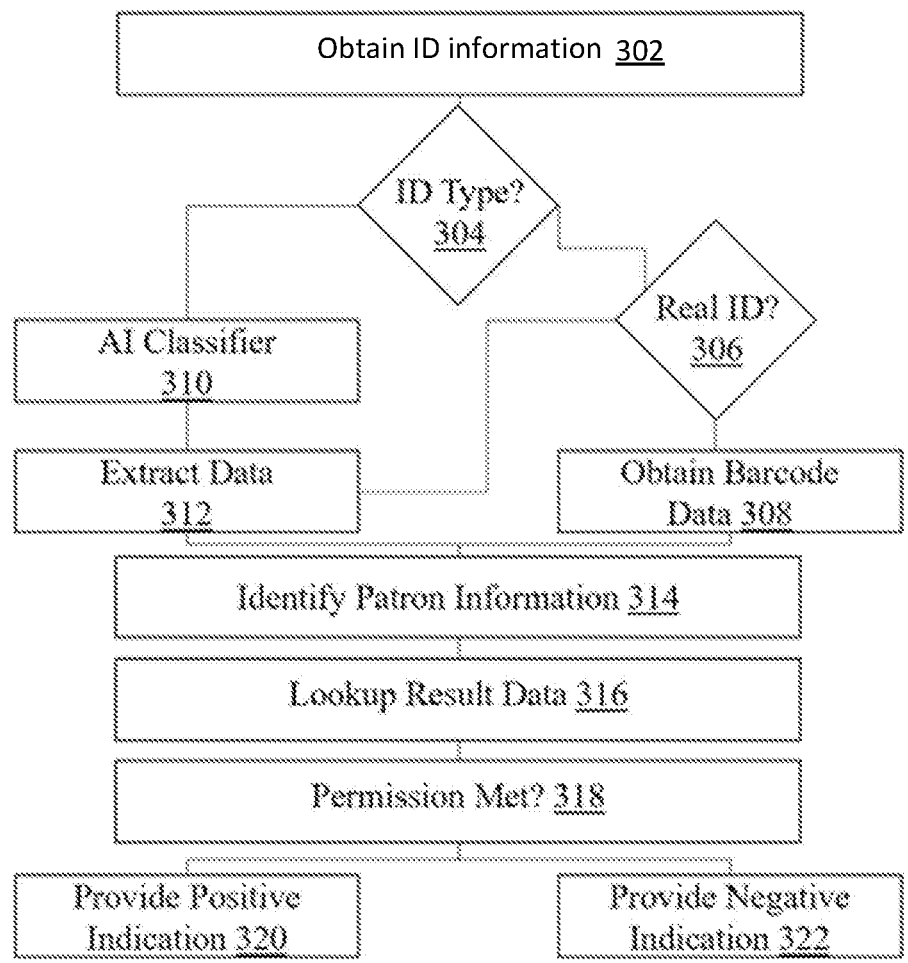
FIG. 5 illustrates an exemplary flowchart of a method in accordance with the disclosure to verify an identity of an individual seeking entry into the establishment.

FIG. 5 illustrates an exemplary flowchart of a method in accordance with the disclosure to verify an identity of the individual 140 seeking entry into the establishment 105. The specific system and method embodied in this process is explained in more detail in FIGS. 3 and 4. As illustrated, the process may begin by obtaining ID information 302 in the form of an ID card or some other identifier from the individual 140. A computing device may determine the ID type 304 by determining whether the obtained data is a government issued identification (such as a driver's license, passport, etc.), or a privately issued identification (such as a workplace issued badge, or a school issued ID). If a government issued ID is identified, the process may further determine if it is a real ID 306. If it is, the process may obtain barcode data 308 to obtain additional information that may be associated with the barcode on the Real ID (if applicable). If the government issued ID is not a Real ID, or if the ID that is supplied by the individual 140 is a privately issued ID, then the data associated with the ID is extracted 312. The data extraction step 312 may retrieve the name, address, and/or other relevant information of the individual 140 that may be necessary to access the test result report of the individual 140. In one embodiment, the process may apply an AI classifier 310 to process privately issued IDs in an effort to extract relevant data more reliably.

In one embodiment, the process may continue by identifying individual information 314 based on the extracted data. As described herein, individual information may include the name, address, medical identifier, etc. of the individual 140. The individual information may be used to lookup the test results data of the individual 140 from a test results database. Alternatively, if a test result report is provided, the process may compare the extracted name and/or other data to corresponding name and/or other data on the test result report to verify that the obtained test result is associated with the individual who is described in the ID. The process may further determine whether the test result data meets the requirements set forth by the establishment 105 by applying computerized analysis 318 as described above. If the individual meets the requirements then a positive indication 320 may be provided to the user device 115. If the individual does not meet the requirements set forth by the establishment, then a negative indication 322 may be provided to the user device 115. As described above, a positive indication 320 may be used to permit entry and a negative indication 322 may be used to deny entry.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 6:
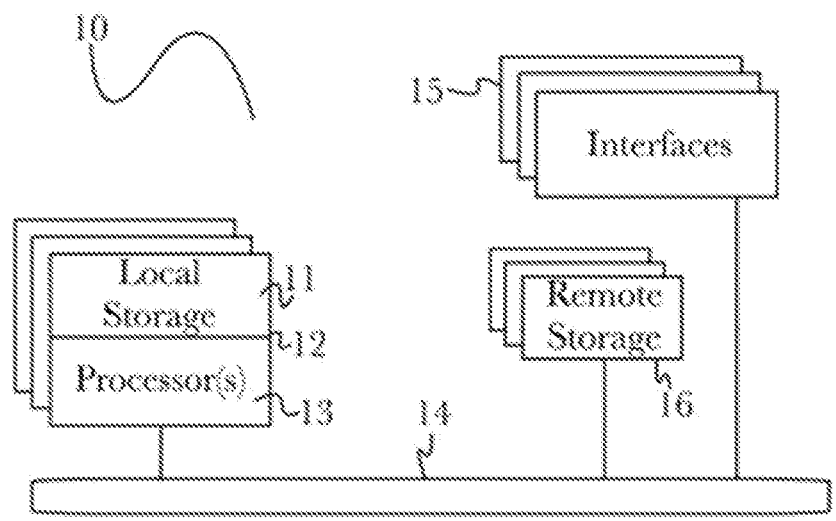
FIG. 6 illustrates some exemplary components that may be included in an entry verification apparatus in accordance with an embodiment of the disclosure.

Referring now to FIG. 6, there is shown a block diagram depicting an exemplary computing device 10 suitable for implementing at least a portion of the features or functionalities disclosed herein. Computing device 10 may be, for example, any one of the computing machines described above, such as, for example, the entry verification apparatus 120, or indeed any other electronic device capable of executing software- or hardware-based instructions according to one or more programs stored in memory. Computing device 10 may be configured to communicate with a plurality of other computing devices, such as clients or servers, over communications networks such as the network 150.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 6 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a user device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memory 11 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 7:
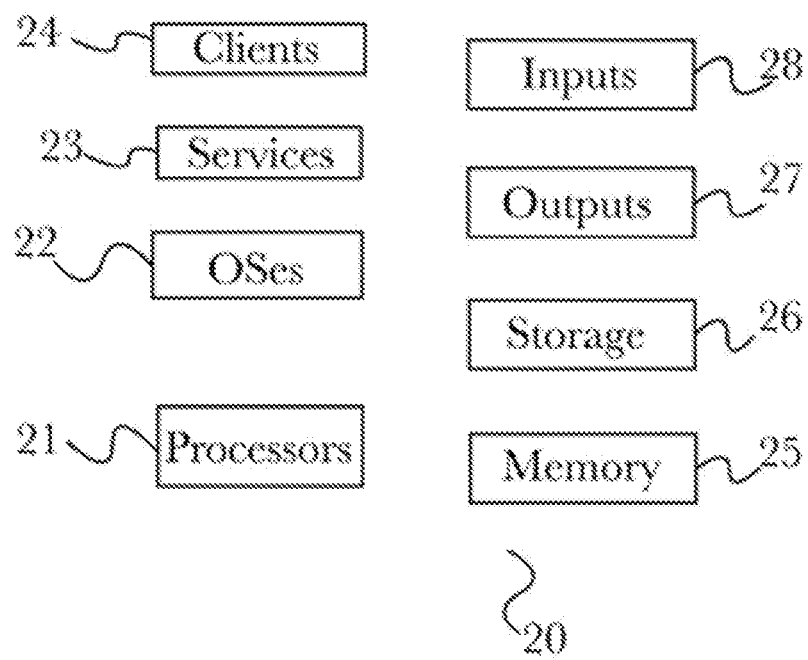
FIG. 7 illustrates some exemplary components that may be included in an entry verification apparatus in accordance with another embodiment of the disclosure.

In some embodiments, systems may be implemented on a standalone computing system. Referring now to FIG. 7, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 5). Examples of storage devices 26 include flash memory, magnetic hard drive, CD-ROM, and/or the like.

Figure 8:
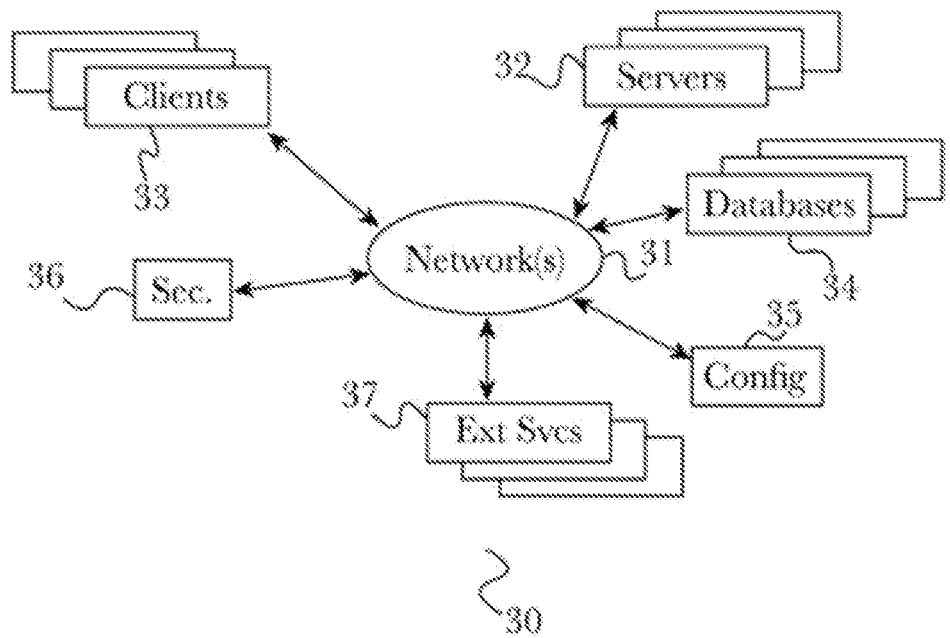
FIG. 8 illustrates an exemplary distributed architecture that may be configured to operate as an entry verification system in accordance with an embodiment of the disclosure.

In some embodiments, systems may be implemented on a distributed computing network, such as one having any number of clients and/or servers. Referring now to FIG. 8, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 7. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

Figure 9:
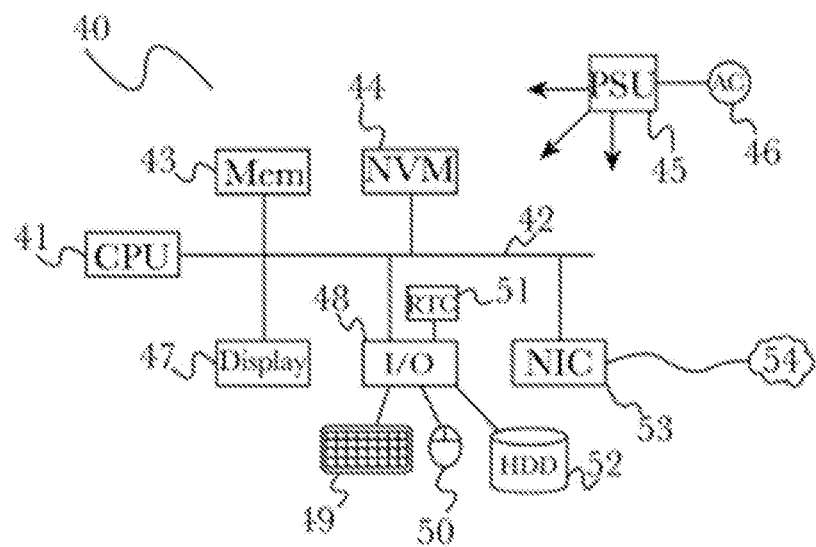
FIG. 9 illustrates an example computer that may be configured to operate as an entry verification apparatus in accordance with an embodiment of the disclosure.

FIG. 9 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

That which is claimed is:

1. A method for determining whether to grant entry to an individual into an establishment, the method comprising:
   receiving, by an entry verification apparatus, digital data associated with the individual;
   obtaining, by the entry verification apparatus, a test result report comprising a digital file that provides an indication whether the individual is one of currently infected by a viral pathogen, previously infected by a viral pathogen, not infected by a viral pathogen, or immunized against a viral pathogen, the test result report provided by at least one of a plurality of test result providers;
   performing character recognition analysis on the digital file to identify at least one component of the test result report, the identification comprising identifying at least a first label associated with at least one of a test and an immunization record that is administered to an individual as indicated in the test result report, wherein another report by at least one of a different test result provider, and a different test type is comprised of a second label that is associated with at least one of a test and an immunization record administered to an individual as indicated in the test result report;
   identifying a spatial disposition of one or more text characters in a template document, wherein identified spatial disposition data is used to at least one of identify components in the template and authenticate the obtained test result;
   identifying additional components in the report based on the template document that is at least associated with reports issued by the at least one of the plurality of test result providers;
   evaluating, by the entry verification apparatus, the received digital data associated with the individual and the identified components of the test result report to verify that the obtained test result report is associated with the individual;
   converting, by the entry verification apparatus, information contained in the test result report into a standardized format by standardizing the first label with a standardized data format and value;
   obtaining, by the entry verification apparatus, entry requirements for enabling entry into the establishment;
   analyzing, by the entry verification apparatus, the standardized information and the entry requirements to determine whether the entry requirements are met;
   determining, by the entry verification apparatus, an entry status based on whether the entry requirements are met; and
   transmitting, by the entry verification apparatus, to a controller of a gate entry system, an activation signal for automatically opening a gate when the entry requirements are met.

2. The method of claim 1, further comprising authenticating the obtained test result report based on at least the identified spatial disposition of one or more text characters in the template document, wherein authenticating the obtained test result report comprises detecting a digital footprint that is indiscernible to human eyes, the digital footprint indicating a tampering of the digital data.

3. The method of claim 1, further comprising verifying an identity of the individual, wherein verifying the identity of the individual comprises:
   identifying a type of an identification provided by the individual;
   when the identification is issued by a government agency, extracting data from the identification and evaluating the data to verify the identity of the individual;
   when the identification is issued by a private entity, verifying an authenticity of the identification; and
   upon confirming the authenticity, verifying the identity of the individual.

4. The method of claim 1, wherein evaluating the received digital data associated with the individual and the identified components of the test result report further comprises evaluating a spatial disposition of a manually-entered text character in the test result report.

5. The method of claim 1, wherein converting to a standardized format comprises identifying information contained in a portion of the test result report and tagging that information with a standardized tag.

6. The method of claim 1, wherein converting to a standardized format comprises at least one of rearranging a first name and a last name of the individual as provided in the test result report, and rearranging a position of a day and a month of a date as provided in the test result report.

7. The method of claim 1, further comprising:
   obtaining, by the entry verification apparatus, a permission from the individual for obtaining the test result report.

8. An entry verification apparatus that determines whether to grant entry to an individual into an establishment, the entry verification apparatus comprising:
   a memory that stores computer-executable instructions; and
   a processor configured to access the memory and execute the computer executable instructions to at least:
   receive digital data associated with the individual;
   obtain a test result report comprising a digital file that provides an indication whether the individual is one of currently infected by a viral pathogen, previously infected by a viral pathogen, not infected by a viral pathogen, or immunized against a viral pathogen, the test result provided by at least one of a plurality of test result providers;
   perform character recognition analysis on the report to identify at least one component of the test result report, the identification comprising identifying at least a first label associated with at least one of a test and an immunization record that is administered to an individual as indicated in the test result report, wherein another report by at least one of a different test result provider, and a different test type is comprised of a second label that is associated with at least one of a test and an immunization record administered to an individual as indicated in the test result report;

identify a spatial disposition of one or more text characters in a template document, wherein identified spatial disposition data is used to at least one of identify components in the template and authenticate the obtained test result;

identify additional components in the report based on the template document that is at least associated with reports issued by the at least one of the plurality of test result providers;

evaluate the received digital and the obtained test result report to verify that the obtained test result report is associated with the individual;

convert information contained in the test result report into a standardized format by standardizing the first label with a standardized data format and value;

obtain entry requirements for enabling entry into the establishment;

analyze the standardized information and the entry requirements to determine whether the entry requirements are met; and determine an entry status based on whether the entry requirements are met; and transmitting an activation signal for automatically opening a gate when the entry requirements are met.

9. The entry verification apparatus of claim 8 wherein the memory and the processor are housed in a server computer that is communicatively coupled to at least one of a user device or a controller in a gate to the establishment.

10. The entry verification apparatus of claim 8, wherein the memory and the processor are housed in a controller of a gate entry system.

11. The entry verification apparatus of claim 8, wherein the processor authenticates the test result report based on the identified spatial disposition of one or more text characters in the template document, wherein authenticating comprises detecting a digital footprint that is indiscernible to human eyes, the digital footprint indicating a tampering of linked to a file comprising the test result report.

12. The entry verification apparatus of claim 11, wherein the processor evaluates a portion of metadata by detecting a digital footprint that is indiscernible to human eyes and indicates a modification having been made upon the file.

13. The entry verification apparatus of claim 8, wherein the processor authenticates the identified components of the test result report by evaluating a spatial disposition and/or a modification of a manually-entered text character in the test result report.

* * * * *